United States Patent [19]
D'Amico

[11] 4,013,638
[45] Mar. 22, 1977

[54] AZABICYCLONONANECARBODITHIOIC ACID

[75] Inventor: John J. D'Amico, Dunbar, W. Va.

[73] Assignee: Monsanto Company, St. Louis, Mo.

[22] Filed: Jan. 18, 1965

[21] Appl. No.: 426,348

[52] U.S. Cl. .................. 260/239 BA; 260/347.2; 260/784; 260/786; 260/791; 260/792

[51] Int. Cl.² ............ C07D 401/12; C07D 403/12; C07D/295/20, C07D 411/12

[58] Field of Search ..260/239 BA, 302H, 306.6R, 326.81, 247.1 L, 293.43, 307.4, 309.2, 347.2, 345.9, 256.5 R, 250 P, 326 S, 326.5 S, 345.1

[56] References Cited
UNITED STATES PATENTS 3,344,134   9/1967   D'Amico .......................... 260/239

FOREIGN PATENTS OR APPLICATIONS 1,426,941   12/1965   France .............................. 260/239

Primary Examiner—Alton D. Rollins

[57] ABSTRACT

Compounds of the formula

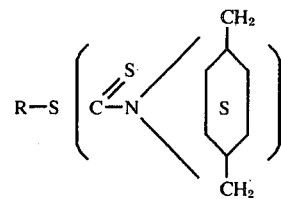

where R is an ester forming radical, salt forming radical, —SCCl₃ or Y—S$_x$ where $x$ is an integer from 0 to 3 and Y is the radical in parentheses. The compounds accelerate vulcanization of natural and synthetic rubber and some have the property of inhibiting oxidation of rubber.

16 Claims, No Drawings

AZABICYCLONONANECARBODITHIOIC ACID

The present invention relates to a new class of products; namely, azabicyclononanecarbodithioic acid and its derivatives. The free dithiocarbamic acid is of limited stability under ordinary conditions, but derivatives are stable.

The new compounds will be more readily understood by reference to the general formula:

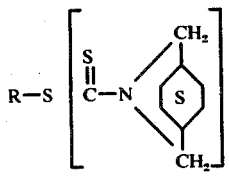

In general R is an ester-forming radical, a salt-forming radical, $SCCl_3$, or $Y - S_x$ where Y is the radical in parenthesis and x is an integer 0 to 3, inclusive. Sulfenamides in which R is an amino radical as described in Example 54 are claimed in co-pending application Ser. No. 463,341 filed June 11, 1965 now abandoned. It will be understood that Y hereinafter means the radical in parentheses.

By salt-forming radical is meant ammonium, substituted ammonium, and metal wherein the metal is alkali metal, alkaline earth metal, $Zn_{1/2}$, $Pb_{1/2}$, $Cu_{1/2}$, $Fe_{1/3}$. The subscripts indicate the reciprocal of the valence of the metal ion because the anion is monovalent. Amines readily form addition salts of the aforesaid dithiocarbamic acid; and where R is substituted ammonium, such amine addition salts are meant. Examples of suitable amines comprise dimethylamine, diethylamine, isopropylamine, diisopropylamine, cyclohexylamine, dicyclohexylamine, pyrrolidine, piperidine, hexamethylenimine, morpholine, and 3-azabicyclo[3.2.2]nonane. Tertiary amines are convenient because they may be present during formation of the dithiocarbamic acid from carbon disulfide without reacting with it, whereas primary and secondary amines react with carbon disulfide. Tertiary amines comprise N,N-dimethylcyclohexylamine, trimethylamine, triethylamine, tributylamine, triethanolamine, and N,N-dimethylaniline.

Esters or organic salts comprise the class of compounds derived by replacing the acid hydrogen of the aforesaid carbodithioic acid with a hydrocarbon radical. This radical, for convenience designated as an ester-forming radical, may contain functional substituents except on the carbon attached to the sulfur, and esters will be understood to refer to this general class. These esters will be better understood by reference to the sub-classes of ester-forming radicals; namely, lower alkyl such as methyl, ethyl, propyl, isopropyl, butyl, isobutyl, amyl, sec. amyl, sec. butyl, and hexyl, substituted alkyl such as cyano-substituted lower alkyl, isothiocyano-substituted lower alkyl, and amino-substituted lower alkyl; namely, lower alkyl substituted by $NH_2$-(N-lower alkylamino)lower alkyl, (N,N-di lower alkylamino)lower alkyl, 1-pyrrolidinyl lower alkyl, piperidino lower alkyl, morpholino lower alkyl, and 1-hexamethyleniminyl lower alkyl. Lower alkenyls (1 to 6 carbon atoms) are desirable ester-forming radicals which class includes halogen-substituted lower alkenyl and cyclohexenyl (2-cyclohexenyl, 3-cyclohexenyl). Diolefinic radicals by which are meant radicals containing two double bonds and 5–10 carbon atoms in the chain herein referred to as alkadienyl, comprise another class of suitable ester-forming radicals; as, for example,

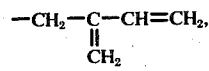

$-CH_2-CH=CH-CH_2CH=CH-CH_3$. The hydrocarbon portion may be divalent; but since R in the general formula is monovalent, such a radical would, for example, be designated as $-CH_2-CH=CH-CH_2CH=CH-CH_2SY$ where Y is the group in parentheses. Again, halogen substitution is included as is also replacement of carbon in the chain by sulfur or oxygen as in $-CH_2CCl=CH-S-CH=CCl-CH_2SY$ and $-CH_2CCl=CH-O-CH=CCl-CH_2SY$.

Other examples of R comprise aryl of the benzene and naphthalene series. By aryl of the benzene and naphthalene series is meant phenyl or naphthyl which may be substituted in the manner indicated and, more particularly, phenyl, tolyl, 1-naphthyl, 2-naphthyl, p-chlorophenyl, p-nitrophenyl, pentachlorophenyl, o-chlorophenyl, and 2,4-dinitrophenyl. Further examples are arylthio lower alkyl where aryl is a member of the benzene and naphthalene series, lower alkynyl like $-CH_2C \equiv CH$ and $-CH_2-C \equiv CCH_3$, and aralkyl, by which is meant aryl attached to lower alkyl. Aryl when attached to lower alkyl means radicals characterized by aromaticity. Radicals having aromaticity mean phenyl, phenyl containing 1–4 lower-alkyl substituents, naphthyl, monochlorophenyl, dichlorophenyl, trichlorophenyl, monobromophenyl, dibromophenyl, tribromophenyl, furyl, pyranyl, and 5-hydroxy-pyranonyl. Aralkyl includes

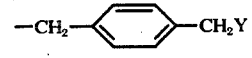

where the phenylene radical may contain 1 to 4 lower-alkyl substituents.

In the general formula R may be an azolyl radical, the carbon of which is attached to sulfur. The resulting compounds are herein regarded as esters of the aforesaid dithiocarbamic acid. By azolyl radical is meant any of the following:
2-benzothiazolyl
2-benzoxazolyl
2-benzimidazolyl
4-lower alkyl-2-benzothiazolyl
5-lower alkyl-2-benzothiazolyl
6-lower alkyl-2-benzothiazolyl
5-chloro-2-benzothiazolyl
4-chloro-2-benzothiazolyl
6-chloro-2-benzothiazolyl
6-nitro-2-benzothiazolyl
7-lower alkyl-2-benzothiazolyl
4-lower alkyl 5-lower alkoxycarbonyl-2-thiazolyl
4-lower alkyl-2-thiazolyl
4,5-di lower alkyl-2-thiazolyl
4,6-di(lower alkyl)diazolyl
4-lower alkyl-5-carbamyl-2-thiazolyl
4-lower alkyl-5-anilinocarbonyl-2-thiazolyl
4-lower alkyl-5-lower acyl-2-thiazolyl
4-carbo lower alkoxy-2-thiazolyl 4,5-di(lower alkyl)-2-benzothiazolyl
4,6-di(lower alkyl)-2-benzothiazolyl
4,6-di(lower alkyl)-7-chloro-2-benzothiazolyl, and
4,6-di(lower alkyl)-5,7-dichloro-2-benzothiazolyl.

Other heterocyclic ester-forming radicals containing nitrogen which are included and hereinafter illustrated are pyrimidinyl, which includes pyrimidinyl containing one or two lower-alkyl substituents, and phthalazinyl.

Another class of ester-forming radicals are —CHYCOR' and CH$_2$COR', where R' is lower alkoxy or an amino radical. In this context amino radicals mean NH$_2$, mono lower alkylamino, di(lower alkyl)amino, 3-azabicyclo[3.2.2]non-3-yl, 1-pyrrolidinyl, piperidino, morpholino, 1-hexamethyleniminyl, N-phenyl N-lower alkylamino, N-(4-anilinophenyl)amino, and N-lower alkyl N-(4-anilinophenyl)amino.

Still another type of functionally substituted ester-forming radicals is imidomethylene by which is meant phthalimidomethylene, succinimidomethylene, maleimidomethylene, and tetrahydrophthalimidomethylene. Thiuram sulfides conform to the general formula wherein R is S$_x$Y —$x$ being an integer from 0 to 3, inclusive. When $x$ is zero, the resulting compound is the thiuram monosulfide; when $x$ is 2, the thiuram disulfide; etc. R may also be SCCl$_3$.

The new compounds are valuable for accelerating vulcanization of natural and synthetic rubber. Some have the property of protecting rubber stocks against the action of oxygen. They may be prepared from 3-azabicyclo[3.2.2]nonane which for convenience will be hereinafter referred to as "amine." The following examples illustrate the preparation and properties but are not to be taken as limitative.

EXAMPLE 1

To a stirred solution containing 12.5 grams (0.1 mole) of amine, 16 grams (0.1 mole) of 25% sodium hydroxide, and 200 ml. of water was added dropwise at 5°–15° C., 7.6 grams (0.1 mole) of carbon bisulfide. The mixture was stirred for an hour at 25°–30° C., then 12.7 grams (0.1 mole) of benzyl chloride added in one portion and heating continued at 50°–60° C. for 5 hours. After cooling to 0° C., the precipitate was collected by filtration, washed with water until the washings were neutral to litmus, and air-dried at 25°–+° C. Benzyl 3-azabicyclo[3.2.2]nonane-3-carbodithioate was obtained in 99% yield as a white solid. After recrystallization from heptane it melted at 98°–99° C. Analysis gave 4.99% nitrogen and 22.00% sulfur compared to 4.80% nitrogen and 22.00% sulfur calculated for C$_{16}$H$_{21}$NS$_2$.

Employing substantially the same reaction conditions and replacing the benzyl chloride with an equimolar amount, respectively, of 2,6-dichlorobenzyl chloride, 3,4-dichlorobenzyl chloride, allyl chloride, 2-bromoallyl chloride, 3-chloro-2-butenyl chloride, cis and trans-2,3-dichloroallyl chloride, 3,3-dichloroallyl chloride, and 3-bromocyclohexene, further examples were prepared possessing the following physical properties.

EXAMPLE 2

2,6-dichlorobenzyl 3-azabicyclo[3.2.2]nonane-3-carbodithioate, a cream solid, m.p. 138°–139° C., after recrystallization from heptane, in 91.5% yield. Analysis gave 4.08% nitrogen, 17.22% sulfur, and 20.15% chlorine compared to 3.88% nitrogen, 17.79% sulfur, and 19.67% chlorine calculated for C$_{16}$H$_{19}$Cl$_2$NS$_2$.

EXAMPLE 3

3,4-Dichlorobenzyl 3-azabicyclo[3.2.2]nonane-3-carbodithioate, an off-white solid, m.p. 111°–113° C., after recrystallization from heptane, in 98.5% yield. Analysis gave 4.31% nitrogen and 17.63% sulfur compared to 3.88% nitrogen and 17.79% sulfur calculated from C$_{16}$H$_{19}$Cl$_2$NS$_2$.

EXAMPLE 4

Allyl 3-azabicyclo[3.2.2]nonane-3-carbodithioate, a white solid, m.p. 56°–57° C., after recrystallization from alcohol, in 99% yield. Analysis gave 6.00% nitrogen and 26.16% sulfur compared to 5.80% nitrogen and 26.56% sulfur calculated for C$_{12}$H$_{19}$NS$_2$.

EXAMPLE 5

2-Bromoallyl 3-azabicyclo[3.2.2]nonane-3-carbodithioate, a brown solid after drying on a porous plate at 25°–30° C. It melted at 71°–73° C. after recrystallization from ethyl alcohol. The yield was 84%. Analysis gave 4.88% nitrogen and 21.73% sulfur compared to 4.37% nitrogen and 20.03% sulfur calculated for C$_{12}$H$_{18}$BrNS$_2$.

EXAMPLE 6

3-Chloro-2-butenyl 3-azabicyclo[3.2.2]nonane-3-carbodithioate, a tan solid, m.p. 84°–85° C., after recrystallization from ethyl alcohol, in 97% yield. Analysis gave 4.80% nitrogen, 21.50% sulfur, and 13.07% chlorine compared to 4.83% nitrogen, 22.12% sulfur, and 12.23% chlorine calculated for C$_{13}$H$_{20}$ClNS$_2$.

EXAMPLE 7 cis and trans-2,3-Dichloroallyl 3-azabicyclo[3.2.2]-nonane-3-carbodithioate, a tan solid after air-drying on a porous plate at 25°–30° C. It melted at 92°–94° C. after recrystallization from ethyl alcohol. The yield was 74%. Analysis gave 4.55% nitrogen, 20.36% sulfur, and 22.70% chlorine compared to 4.51% nitrogen, 20.66% sulfur, and 22.85% chlorine calculated for C$_{12}$H$_{17}$Cl$_2$NS$_2$.

EXAMPLE 8

3,3-Dichloroallyl 3-azabicyclo[3.2.2]nonane-3-carbodithioate, a tan solid after air-drying on a porous plate. It melted at 68°–70° C. after recrystallization from ethyl alcohol. The yield was 74.5%. Analysis gave 5.11% nitrogen and 21.60% sulfur compared to 4.51% nitrogen and 20.66% sulfur calculated for C$_{12}$H$_{17}$Cl$_2$NS$_2$.

EXAMPLE 9

2-Cyclohexen-1-yl 3-azabicyclo[3.2.2]nonane-3-carbodithioate, a cream solid, m.p. 80°–82° C., after recrystallization from ethyl alcohol, in 82.2% yield. Analysis gave 5.30% nitrogen and 22.83% sulfur compared to 4.97% nitrogen and 22.78% sulfur calculated for C$_{15}$H$_{23}$NS$_2$.

Replacing the benzyl chloride of Example 1 with an equimolar amount, respectively, of 2,3,3-trichloroallyl chloride, 2-chloroallyl chloride, and 2,3,6-trichlorobenzyl chloride, further examples were prepared as follows. In these examples the slurry of amine, sodium hydroxide, and water was stirred at 5°–10° C. while adding the carbon bisulfide.

EXAMPLE 10

2,3,3-Trichloroallyl 3-azabicyclo[3.2.2]nonane-3-carbodithioate, a brown solid, m.p. 62°–63° C., after recrystallization from ethyl alcohol, in 98.5% yield. Analysis gave 4.27% nitrogen, 18.56% sulfur, and 30.37% chlorine compared to 4.06% nitrogen, 18.60% sulfur, and 30.85% chlorine calculated for $C_{12}H_{16}Cl_3NS_2$.

EXAMPLE 11

2-Chloroallyl 3-azabicyclo[3.2.2]nonane-3-carbodithioate, a tan solid, m.p. 88°–π° C., after recrystallization from heptane, in 98% yield. Analysis gave 22.75% sulfur and 13.06% chlorine compared to 23.25% sulfur and 12.85% chlorine calculated for $C_{12}H_{18}ClNS_2$.

EXAMPLE 12

2,3,6-Trichlorobenzyl 3-azabicyclo[3.2.2]nonane-3-carbodithioate, a yellow solid, m.p. 113°–115° C., after recrystallization from alcohol, in 96.5% yield. Analysis gave 3.41% nitrogen and 15.71% sulfur compared to 3.55% nitrogen and 16.24% sulfur calculated from $C_{16}H_{18}Cl_3NS_2$.

EXAMPLE 13

Substituting an equimolar amount of ar,ar,ar-trichlorobenzyl chloride for the benzyl chloride in Example 1, the product was cooled to 5° C., then 200 ml. of ethyl ether added and stirring continued at 0°–5° C. for 15 minutes. The precipitate was collected by filtration and air-dried. ar,ar,ar-Trichlorobenzyl 3-azabicyclo[3.2.2]nonane-3-carbodithioate was obtained as a white solid melting at 145°–150° C. after recrystallization from heptane. Analysis gave 3.30% nitrogen, 15.47% sulfur, and 27.80% chlorine compared to 3.55% nitrogen, 16.24% sulfur, and 26.94% chlorine calculated for $C_{16}H_{18}Cl_3NS_2$.

EXAMPLE 14

Substituting an equimolar amount of 3-bromo-1-propyne for the benzyl chloride in Example 1, the product was cooled to 25 C. and extracted with 300 ml. of ethyl ether. The ether solution was separated, washed with water until the washings were neutral to litmus, and dried over sodium sulfate. Ether was removed in vacuo at a maximum temperature of 30° C./1–2 mm. 2-Propynyl 3-azabicyclo[3.2.2]nonane-3-carbodithioate was obtained in 79% yield as a viscous black oil. Analysis gave 5.54% nitrogen and 27.21% sulfur compared to 5.85% nitrogen and 26.79% sulfur calculated for $C_{12}H_{17}NS_2$.

EXAMPLE 15

In the procedure of Example 1, an equimolar amount of 2(diethylamino)ethyl chloride hydrochloride in 16 grams (0.1 mole) of 25% sodium hydroxide was substituted for the benzyl chloride of the example. 2(Diethylamino)ethyl 3-azabicyclo[3.2.2]nonane-3-carbodithioate was obtained in 99% yield as a grey solid melting at 37°–39° C. Analysis gave 8.60% nitrogen compared to 9.32% calculated for $C_{15}H_{28}N_2S_2$.

Replacing the 2(diethylamino)ethyl chloride hydrochloride of Example 15 with the appropriate amine reactant, further examples possessing the following physical properties were prepared:

EXAMPLE 16

2-(Diisopropylamino)ethyl 3-azabicyclo[3.2.2]nonane-3-carbodithioate, a yellow solid, m.p. 60°–61° C., after recrystallization from alcohol, in 97.5% yield. Analysis gave 8.48% nitrogen and 19.74% sulfur compared to 8.53% nitrogen and 19.52% sulfur calculated for $C_{17}H_{32}N_2S_2$.

EXAMPLE 17

2-(Dimethylamino)ethyl 3-azabicyclo[3.2.2]nonane-3-carbodithioate, a white solid, m.p. 130°–132° C., after recrystallization from alcohol, in 88% yield. Analysis gave 23.08% sulfur compared to 23.54% calculated for $C_{13}H_{24}N_2S_2$.

EXAMPLE 18

3-(Dimethylamino)propyl 3-azabicyclo[3.2.2]nonane-3-carbodithioate, a white solid, m.p. 114°–116° C., after recrystallization from ethyl acetate, in 90.5% yield. Analysis gave 9.02% nitrogen compared to 9.78% calculated for $C_{14}H_{26}N_2S_2$.

EXAMPLE 19

To a stirred solution containing 12.5 grams (0.1 mole) of amine, 16 grams (0.1 mole) of 25% sodium hydroxide, and 200 ml. of water was added dropwise at 5°–15° C., 7.6 grams (0.1 mole) of carbon bisulfide. The mixture was stirred for an hour at 25°–30° C., then 15.8 grams (0.1 mole) of 2-dimethylamino-1-methylethyl chloride hydrochloride in 16 grams (0.1 mole) of 25% sodium hydroxide added in one portion and the mixture heated at 50°–56° C. for 5 hours. After cooling to 25° C., the reaction mixture was extracted with 400 ml. of ethyl ether, the ether solution washed with water until the washings were neutral to litmus, and dried over sodium sulfate. Ether was removed in vacuo at a maximum temperature of 80°–90° C./1–2 mm. 22-(Dimethylamino)-1-methylethyl 3-azabicyclo[3.2.2]nonane-3-carbodithioate was obtained in 84% yield as a viscous amber oil. Analysis gave 9.89% nitrogen and 22.25% sulfur compared to 9.77% nitrogen and 22.38% sulfur calculated for $C_{14}H_{26}N_2S_2$.

Substituting the appropriate amine reactant in the procedure of Example 19, further examples were prepared as follows:

EXAMPLE 20

3-(Dimethylamino)-2-methylpropyl 3-azabicyclo[3.2.2]-nonane-3-carbodithioate, a viscous amber oil, in 56.5% yield. Analysis gave 10.00% nitrogen and 20.80% sulfur compared to 9.32% nitrogen and 21.34% sulfur calculated for $C_{15}H_{28}N_2S_2$.

EXAMPLE 21

3-(Diethylamino)propyl 3-azabicyclo[3.2.2]nonane-3-carbodithioate, a black oil, in 73% yield. Analysis gave 8.76% nitrogen and 20.57% sulfur compared to 8.91% nitrogen and 20.39% sulfur calculated for $C_{16}H_{30}N_2S_2$.

EXAMPLE 22

To a stirred solution containing 12.5 grams (0.1 mole) of amine, 16 grams (0.1 mole) of 25% sodium hydroxide, and 200 ml. of water was added dropwise at 5°–15° C., 7.6 grams (0.1 mole) of carbon bisulfide. The mixture was stirred at 25°–30° C. for an hour, then 18.9 grams (0.1 mole) of 1,1,2-trifluoro-4-bromo-1- butene was added in one portion, and heating continued at 50°–60° C. for 4 hours. After cooling to 25° C., the stirred reaction mixture was extracted with 400 ml. of ethyl ether, the ether solution separated, washed with water until the washings were neutral to litmus, and dried over sodium sulfate. Ether was removed in vacuo at a maximum temperature of 80°–90° C/1–2 mm. 3,4,4-Trifluoro-3-butenyl 3-azabicyclo[3.2.2]nonane-3-carbodithioate was obtained in 80.5% yield as a black oil. Analysis gave 4.68% nitrogen and 20.19% sulfur compared to 4.53% nitrogen and 20.73% sulfur calculated for $C_{13}H_{18}F_3NS_2$.

EXAMPLE 23

To a stirred solution containing 12.5 grams (0.1 mole) of amine, 16 grams (0.1 mole) of 25% sodium hydroxide, and 200 ml. of ethyl alcohol was added dropwise at 5°–15° C., 7.6 grams (0.1 mole) of carbon bisulfide. The mixture was stirred at 25°–30° C. for an hour, then 12.3 grams (0.1 mole) of ethyl chloroacetate added, and stirring continued at 25°–30° C. for 24 hours. Thereupon there was added 400 ml. of ethyl ether and 300 ml. of water and stirring continued for 15 minutes. The ether layer was then separated, washed with water until the washings were neutral to litmus, and dried over sodium sulfate. Ether was removed in vacuo and the product air-dried at 25°–30° C. Ethyl mercaptoacetate, 3-azabicyclo[3.2.2]nonane-3-carbodithioate was obtained in 90.5% yield as a yellow solid melting at 48°–49° C., after recrystallization from ethyl alcohol. Analysis gave 5.03% nitrogen and 22.68% sulfur compared to 4.87% nitrogen and 22.31% sulfur calculated for $C_{13}H_{21}NO_2S_2$.

EXAMPLE 24

To a stirred solution containing 50 grams (0.4 mole) of amine and 500 ml. of ethyl ether was added dropwise in 10 minutes at 0°–10° C., 23 grams (0.2 mole) of thiophosgene. The mixture was then stirred at 25°–30° C. for 5 hours, 500 ml. of water added, and stirring continued for 15 minutes. The impurities were then removed by filtration. The ether layer which separated was washed with water until the washings were neutral to litmus and dried over sodium sulfate. Ether was removed in vacuo at a maximum temperature of 30° C./10–12 mm., and the solid air-dried at 25°–30° C. Thio-3-azabicyclo[3.2.2]nonane-3-carbonyl chloride was obtained in 61.6% yield as a light tan solid melting at 89°–90° C. after recrystallization from heptane/benzene. Analysis gave 6.84% nitrogen, 15.60% sulfur, and 17.30% chlorine compared to 6.88% nitrogen, 15.74% sulfur, and 17.41% chlorine calculated for $C_9H_{14}ClNS$.

To a stirred solution comprising 25.5 grams (0.15 mole) of 2-mercaptobenzothiazole (99% purity), 500 ml. of acetone, 10 ml. of water, and 9.9 grams (0.15 mole) of 85% potassium hydroxide was added in one portion 30.6 grams (0.15 mole) of the above thio-3-azabicyclo[3.2.2]nonane-3-carbonyl chloride. The mixture was stirred at 25°–30° C. for 5 hours, 500 ml. of water then added, and stirring continued for 30 minutes. The precipitate was collected by filtration, washed with water until the washings were neutral to litmus, and dried at 25°–30° C. 2-Benzothiazolyl 3-azabicyclo[3.2.2]nonane-3-carbodithioate was obtained in 94% yield as a light tan solid melting at 177°–178° C. after recrystallization from acetone. Analysis gave 8.48% nitrogen and 28.60% sulfur compared to 8.38% nitrogen and 28.76% sulfur calculated for $C_{16}H_{18}N_2S_3$.

EXAMPLE 25

An equimolar amount of 5-chloro-2-mercaptobenzothiazole was substituted for 2-mercaptobenzothiazole in the procedure of the second paragraph of Example 24. 5-Chloro-2-benzothiazolyl 3-azabicyclo[3.2.2]nonane-3-carbodithioate was obtained in 91% yield as a light tan solid melting at 180°–181° C. after a second recrystallization from ethyl acetate. Analysis gave 26.14% sulfur and 10.00% chlorine compared to 26.07% sulfur and 9.61% chlorine calculated for $C_{16}H_{17}ClN_2S_3$.

EXAMPLE 26

In the procedure of the second paragraph of Example 24, a solution containing 21.2 grams (0.1 mole) of 6-ethoxy mercaptobenzothiazole, 400 ml. of acetone, 10 ml. of water, and 6.6 grams (0.1 mole) of 85% potassium hydroxide was added to 20.4 grams (0.1 mole) of the thio-3-azabicyclo[3.2.2]nonane-3-carbonyl chloride prepared above. 6-Ethoxy-2-benzothiazolyl 3-azabicyclo[3.2.2]nonane-3-carbodithioate was obtained in 95% yield as a brown solid melting at 161°–163° C. after recrystallization from ethyl acetate. Analysis gave 7.78% nitrogen and 25.53% sulfur compared to 7.40% nitrogen and 25.41% sulfur calculated for $C_{18}H_{22}N_2OS_3$.

EXAMPLE 27

To a stirred solution containing 20.4 grams (0.1 mole) of ethyl 2-mercapto-4-methyl-5-thiazolecarboxylate, 300 ml. of acetone, 10 ml. of water, and 6.6 grams (0.1 mole) of 85% potassium hydroxide was added in one portion 20.4 grams (0.1 mole) of the thio-3-azabicyclo[3.2.2]nonane-3-carbonyl chloride prepared above. The mixture was stirred at 25°–30° C. for 4 hours, 600 ml. of water then added, and stirring continued for an hour at the same temperature. The precipitate was collected by filtration, washed with water until the washings were neutral to litmus, and air-dried at 25°–30° C. Ethyl 2-mercapto-4-methyl-5-thiazolecarboxylate, 3-azabicyclo[3.2.2]nonane-3-carbodithioate was obtained in 99% yield as a tan solid melting at 119°–120° C., after recrystallization from alcohol. Analysis gave 8.04% nitrogen and 26.15% sulfur compared to 7.56% nitrogen and 25.96% sulfur calculated for $C_{16}H_{22}N_2O_2S_3$.

Replacing the ethyl 2-mercapto-4-methyl-5-thiazolecarboxylate of Example 27 with an equimolar amount, respectively, of 4-methyl-2-mercaptothiazole and 2-mercapto-4-methyl-5-anilinocarbonylthiazole, further examples were prepared possessing the following physical properties.

EXAMPLE 28

4-Methyl-2-thiazolyl 3-azabicyclo[3.2.2]nonane-3-carbodithioate, a tan solid, m.p. 173°–174° C., after recrystallization from alcohol, in 97% yield. Analysis gave 9.79% nitrogen and 31.93% sulfur compared to 9.39% nitrogen and 32.23% sulfur calculated for $C_{13}H_{18}N_2S_3$.

EXAMPLE 29

4-Methyl-5-(phenylcarbamoyl)-2-thiazolyl 3-azabicyclo[3.2.2]nonane-3-carbodithioate, a solid melting at 218°–220° C., after recrystallization from dimethyl formamide, in 96% yield. Analysis gave 10.21% nitrogen and 22.62% sulfur compared to 10.06% nitrogen and 23.04% sulfur calculated for $C_{20}H_{23}N_3OS_3$.

EXAMPLE 30

To a stirred solution containing 15.1 grams (0.1 mole) of 2-mercaptobenzoxazole, 400 ml. of acetone, 10 ml. of water, and 6.6 grams (0.1 mole) of 85% potassium hydroxide was added in one portion 20.4 grams (0.1 mole) of the thio-3-azabicyclo-[3.2.2]nonane-3-carbonyl chloride prepared above. The mixture was stirred at 25°–30° C. for 5 hours, 600 ml. of water then added, and stirring continued at the same temperature for 30 minutes. The precipitate was collected by filtration, washed with water until the washings were neutral to litmus, and air-dried at 25°–30° C. 2-Benzoxazolyl 3-azabicyclo[3.2.2]nonane-3-carbodithioate was obtained in 87.5% yield as a brown solid melting at 174°–175° C. after recrystallization from ethyl acetate. Analysis gave 8.85% nitrogen and 20.03% sulfur compared to 8.80% nitrogen and 20.14% sulfur calculated for $C_{16}H_{18}N_2OS_2$.

Employing substantially the same reaction conditions as in Example 30 and replacing the 2-mercaptobenzoxazole with an equimolar amount, respectively, of 2-mercaptobenzimidazole, 6-nitro-2-mercaptobenzothiazole, 4,6-dimethyl 2-pyrimidinethiol hydrochloride, 2-mercapto-4-methyl 5-thiazole carboxamide, and 2-mercapto-4-methyl-5-thiazolyl methyl ketone, further examples were prepared possessing the following physical properties.

EXAMPLE 31

2-Benzimidazolyl 3-azabicyclo[3.2.2]nonane-3-carbodithioate, a cream solid, m.p. 206°–208° C., after recrystallization from alcohol, in 85% yield. Analysis gave 13.18% nitrogen and 20.55% sulfur compared to 13.24% nitrogen and 20.20% sulfur calculated for $C_{16}H_{19}N_3S_2$.

EXAMPLE 32

6-Nitro-2-benzothiazolyl 3-azabicyclo[3.2.2]nonane-3-carbodithioate, an orange solid, m.p. 183°–184° C., after recrystallization from acetone, in 73.5% yield. Analysis gave 10.85% nitrogen and 25.21% sulfur compared to 11.07% nitrogen and 25.35% sulfur calculated for $C_{16}H_{17}N_3O_2S_3$.

EXAMPLE 33

4,6-Dimethyl-2-pyrimidinyl 3-azabicyclo[3.2.2]nonane-3-carbodithioate, a cream solid, m.p. 108°–110° C., after recrystallization from alcohol, in 65% yield. Analysis gave 21.05% sulfur compared to 20.86% calculated for $C_{15}H_{21}N_3S_2$.

EXAMPLE 34

5-Carbamoyl-4-methyl-2-thiazolyl 3-azabicyclo[3.2.2]-nonane-3-carbodithioate, a tan solid, m.p. 178°–180° C., after recrystallization from alcohol, in 73% yield. Analysis gave 27.83% sulfur compared to 28.17% calculated for $C_{14}H_{19}N_3OS_3$.

EXAMPLE 35

5-Acetyl-4-methyl-2-thiazolyl 3-azabicyclo[3.2.2]-nonane-3-carbodithioate, a brown solid, m.p. 80°–82° C., after recrystallization from alcohol, in 76.4% yield. Analysis gave 8.28% nitrogen and 27.64% sulfur compared to 8.23% nitrogen and 28.25% sulfur calculated for $C_{15}H_{20}N_2OS_3$.

EXAMPLE 36

To a stirred solution containing 12.5 grams (0.1 mole) of amine, 200 ml. of ethyl alcohol, and 16 grams (0.1 mole) of 25% sodium hydroxide was added dropwise at 5°–15° C., 7.6 grams (0.1 mole) of carbon bisulfide. The mixture was stirred at 25°–30° C. for an hour, then 19.3 grams (0.1 mole) of p-chlorophenyl chloromethyl sulfide were added dropwise in 20 minutes causing the temperature to rise from 30° to 41° C. The mixture was stirred at 25°–30° C. for 4 hours, 500 ml. of water then added, the product cooled to 5° C., and held at 0°–5° C. for one hour. The precipitate was collected by filtration and air-dried at 25°–30° C. (p-Chlorophenylthio)methyl 3-azabicyclo[3.2.2]-nonane-3-carbodithioate was obtained in 98% yield as an off-white solid melting at 75°–76° C. after recrystallization from alcohol. Analysis gave 4.11% nitrogen, 26.87% sulfur, and 10.05% chlorine compared to 3.91% nitrogen, 26.87% sulfur, and 9.90% chlorine calculated for $C_{16}H_{20}ClNS_3$.

EXAMPLE 37

Substituting 4-tert. butyl phenyl chloromethyl sulfide for the sulfide in Example 36, the temperature rose from 30° to 40° C. (p-tert-Butylphenylthio)methyl 3-azabicyclo[3.2.2]nonane-3-carbodithioate was obtained in 97.5% yield as an off-white solid melting at 67°–68° C. after recrystallization from alcohol. Analysis gave 3.50% nitrogen and 24.75% sulfur compared to 3.69% nitrogen and 25.34% sulfur calculated for $C_{20}H_{29}NS_3$.

EXAMPLE 38

Substituting p-methylphenyl chloromethyl sulfide for the sulfide in Example 36, the temperature rose from 25° to 36° C. (p-Tolylthio)methyl 3-azabicyclo[3.2.2-]nonane-3-carbodithioate was obtained in 97.5% yield as an off-white solid melting at 81°–82° C., after recrystallization from heptane. Analysis gave 3.87% nitrogen and 28.34% sulfur compared to 4.15% nitrogen and 28.50% sulfur calculated for $C_{17}H_{23}NS_3$.

EXAMPLE 39

Replacing the p-chlorophenyl chloromethyl sulfide of Example 36 with an equimolar amount of phenyl chloromethyl sulfide, the temperature rose from 25° to 35° C. After stirring the mixture at 25°–30° C. for 4 hours, there was added 400 ml. of water, and 500 ml. of ethyl ether and stirring continued for 15 minutes. The ether layer which separated was washed with water until neutral to litmus and dried over sodium sulfate. Ether was removed in vacuo at a maximum temperature of 30° C./1–2 mm. The (phenylthio)methyl 3-azabicyclo[3.2.2]nonane-3-carbodithioate was air-dried on a porous plate. The yield was 80.5% of an off-white solid melting at 57°–58° C. after recrystallization from alcohol. Analysis gave 4.21% nitrogen and 29.77% sulfur compared to 4.33% nitrogen and 29.73% sulfur calculated for $C_{16}H_{21}NS_3$.

EXAMPLE 40

To a stirred solution containing 25.0 grams (0.2 mole) of amine, 600 ml. of ethyl alcohol, 10 ml. of water, and 13.2 grams (0.2 mole) of 85% potassium hydroxide was added dropwise at 5°–15° C., 15.2 grams (0.2 mole) of carbon bisulfide and the mixture stirred at 25°–30° C. for an hour. Thereupon there was added in one portion 32.2 grams (0.2 mole) of chlorokojic acid. The product was heated at 75°–80° C. for 6 hours, at 25°–30° C. for 18 hours, and then added to 2,000 grams of ice-water. After stirring for an hour, the precipitate was collected by filtration, washed with water until the washings were neutral to litmus, and air-dried at 25°–30° C. 5-Hydroxy-4-oxo-4H-pyram-2-ylmethyl 3-azabicyclo[3.2.2]nonane-3-carbodithioate was obtained in 99% yield as a cream solid melting at 206°–208° C. after recrystallization from dimethyl formamide. Analysis gave 4.28% nitrogen compared to 4.30% calculated for $C_{15}H_{19}NO_3S_2$.

EXAMPLE 41

To a stirred solution containing 37.5 grams (0.3 mole) of amine, 48 grams (0.3 mole) of 25% sodium hydroxide, and 300 ml. of water there was added dropwise at 5°–15° C., 22.8 grams (0.3 mole) of carbon bisulfide. After stirring for one hour at 25°–30° C. there was added in one portion 15.9 grams (0.3 mole) of acrylonitrile and stirring continued at 25°–30° C. for 6 hours. The precipitate was collected by filtration, washed with water until the washings were neutral to litmus, and air-dried at 25°–30° C. 2-Cyanoethyl 3-azabicyclo[3.2.2]nonane-3-carbodithioate was obtained in 81.9% yield as a white solid melting at 88°–89° C. after recrystallization from alcohol. Analysis gave 11.07% nitrogen and 25.71% sulfur compared to 11.01% nitrogen and 25.21% sulfur calculated for $C_{12}H_{18}N_2S_2$.

EXAMPLE 42

To a stirred solution containing 15 grams (0.12 mole) of amine, 19.2 grams (0.12 mole) of 25% sodium hydroxide and 250 ml. of acetone there was added dropwise at 5°–15° C., 9.2 grams (0.12 mole) of carbon bisulfide. After stirring at 25°–30° C. for an hour, 19.6 grams (0.1 mole) of phthalimidomethyl chloride was added in one portion and stirring continued at 25°–30° C. for another hour. Thereupon there was added 700 ml. of water and the reaction mixture stirred and cooled to 5° C. The product was isolated as described in Example 41. Phthalimidomethyl 3-azabicyclo[3.2.2]nonane-3-carbodithioate was obtained in 99% yield as a grey solid melting at 139°–140° C. after recrystallization from ethyl alcohol/benzene. Analysis gave 7.46% nitrogen and 18.09% sulfur compared to 7.77% nitrogen and 17.79% sulfur calculated for $C_{18}H_{20}N_2O_2S_2$.

EXAMPLE 43

To a stirred solution containing 12.5 grams (0.1 mole) of amine, 16 grams (0.1 mole) of 25% sodium hydroxide, and 200 ml. of water was added dropwise at 5°–15° C., 7.6 grams (0.1 mole) of carbon bisulfide. The mixture was stirred at 25°–30° C. for an hour, 16.5 grams (0.1 mole) of 1-phthalazino chloride was added in one portion and heating continued at reflux (75°–80° C.) for 24 hours. The product was then cooled to 25° C., 600 grams of ice-water added, stirring continued at 0°–10° C. for 15 minutes, and the precipitate collected by filtration, washed with water until the washings were neutral to litmus, and air-dried at 25°–30° C. 1Phthalazinyl 3-azabicyclo[3.2.2]nonane-3-carbodithioate was obtained in 97% yield as a yellow solid melting at 150°–151° C. after recrystallization from dimethyl formamide. Analysis gave 12.58% nitrogen and 19.03% sulfur compared to 12.75% nitrogen and 19.46% sulfur calculated for $C_{17}H_{19}N_3S_2$.

EXAMPLE 44

To a stirred solution containing 12.5 grams (0.1 mole) of amine, 16 grams (0.1 mole) of 25% NaOH, 300 ml. of acetone, and 10 ml. of water was added dropwise at 5°–15° C., 7.6 grams (0.1 mole) of carbon bisulfide. After stirring at 25°–30° C. for an hour, 21.2 grams (0.1 mole) of N-isopropyl-N-anilino carbonylmethyl chloride was added in one portion and the mixture heated at reflux for 6 hours and then at 25°–30° C. for 18 hours. Thereupon there was added 600 ml. of water and stirring continued at 0°–10° C. for an hour after which the product was isolated as described in Example 41. N-Isopropyl-N-anilino carbonylmethyl azabicyclo[3.2.2]nonane-3-carbodithioate was obtained in 99% yield as a cream solid melting at 140°–141° C. after recrystallization from alcohol. Analysis gave 7.23% nitrogen and 16.99% sulfur compared to 7.44% nitrogen and 17.03% sulfur calculated for $C_{20}H_{28}N_2OS_2$.

Employing substantially the same reaction conditions and replacing the N-isopropyl-N-anilino carbonylmethyl chloride with an equimolar amount, respectively, of diethylamino carbonylmethyl chloride and methylamino carbonylmethyl chloride, further examples were prepared possessing the following physical properties.

EXAMPLE 45

Diethylamino carbonylmethyl 3-azabicyclo[3.2.2]nonane-3-carbodithioate, a light tan solid, m.p. 85°–86° C., after recrystallization from dilute alcohol, in 96% yield. Analysis gave 8.59% nitrogen and 20.70% sulfur compared to 8.91% nitrogen and 20.39% sulfur calculated for $C_{15}H_{26}N_2OS_2$.

EXAMPLE 46

Methylamino carbonylmethyl 3-azabicyclo[3.2.2]nonane-3-carbodithioate, an off-white solid, m.p. 126°–127° C., after recrystallization from alcohol, in 99% yield. Analysis gave 10.04% nitrogen and 23.39% sulfur compared to 10.28% nitrogen and 23.54% sulfur calculated for $C_{12}H_{20}N_2OS_2$.

EXAMPLE 47

N-Chloromethylcarbonyl-3-azabicyclo[3.2.2]nonane required as a starting material in this example was prepared substantially as described in copending Application Ser. No. 278,997, filed May 8, 1963, A mixture of 125 grams (1.0 mole) of amine, 101.3 grams (1.0 mole) of triethylamine, and 1500 ml. of ethyl ether was prepared and 113 grams (1.0 mole) of chloroacetyl chloride added dropwise over a period of 15 minutes. The temperature during the addition was maintained at 25°–30° C. by means of an ice-bath. Stirring was continued at this same temperature for 24 hours, a liter of water added, and stirring continued for an additional 15 minutes. The ether layer was washed with water until the washings were neutral to litmus and dried over sodium sulfate. The ether was removed in vacuo at a maximum temperature of 30° C./10–12 mm. and the resulting solid air-dried at 25°–30° C.

To a stirred solution comprising 12.5 grams (0.1 mole) of amine, 6.6 grams (0.1 mole) of 85% potassium hydroxide, 300 ml. of acetone, and 10 ml. of water was added dropwise at 5°–15° C., 7.6 grams (0.1 mole) of carbon bisulfide. After stirring at 25°–30° C. for an hour, 20.2 grams (0.1 mole) of the N-chloromethyl carbonyl-3-azabicyclo[3.2.2]nonane described in the preceding paragraph was added in one portion and the mixture heated at 55°–56° C. for 4 hours. After cooling to 0° C., 600 grams of ice-water was added, stirring continued at 0°–10° C. for 30 minutes, and the product isolated as described in Example 41. 2-(3-Azabicyclo[3.2.2]non-3-yl)-2-oxoethyl 3-azabicyclo[3.2.2]-nonane-3-carbodithioate was obtained in 95% yield as a white solid melting at 131°–132° C. after recrystallization from ethyl acetate. Analysis gave 7.71% nitrogen compared to 7.64% calculated for $C_{19}H_{30}N_2OS_2$.

EXAMPLE 48

N-Hexamethylene-α-chloroacetamide required as an intermediate in this example was prepared according to the procedure for the starting material in Example 47 but substituting N-hexamethylenimine. The ether was removed in vacuo at a maximum temperature of 80°–90° C./10–12 mm., and the product was an oil obtained in 63.5% yield.

Employing substantially the same reaction conditions as described in the second paragraph of Example 47 and replacing N-chloromethyl carbonyl-3-azabicyclo[3.2.2]nonane with an equimolar amount of the N-hexamethylene-α-chloroacetamide prepared above, the product was heated at 50°–56° C. for 4 hours and isolated as described. 2-(Hexahydro-1H-azepin-1-yl)-2oxoethyl 3-azabicylco[3.2.2]nonane-3-carbodithioate was obtained in 99% yield as a yellow orange solid melting at 108°–109° C. after recrystallization from alcohol. Analysis gave 8.11% nitrogen and 18.82% sulfur compared to 8.23% nitrogen and 18.83% sulfur calculated for $C_{17}H_{28}N_2OS_2$.

EXAMPLE 49

The N-chloroacetyl-N'-phenyl-p-phenylenediamine used as a starting material in this example was prepared as follows: A mixture of 36.2 grams (0.2 mole) of N-phenyl-p-phenylenediamine, 20.3 grams (0.2 mole) of triethylamine, and 700 ml. of ethyl ether was prepared and 22.6 grams (0.2 mole) of chloroacetyl chloride added dropwise at 25°–30° C. with ice cooling. Stirring was continued at 25°–30° C. for 24 hours, 400 ml. of water added, and stirring continued for an additional 15 minutes. The ether solution was washed with water until the washings were neutral to litmus and dried over sodium sulfate. The ether was removed in vacuo at a maximum temperature of 30° C./10–12mm., and the resulting solid dried on a porous plate. The product was obtained in 94.5% yield melting at 128°–129° C. after recrystallization from dilute alcohol. Analysis gave 10.72% nitrogen and 13.49% chlorine compared to 10.75% nitrogen and 13.60% chlorine calculated for $C_{14}H_{13}ClN_2O$.

To a stirred solution containing 11.2 grams (0.0885 mole) of amine, 5.6 grams (0.0885 mole) of 85% potassium hydroxide, 200 ml. of ethyl alcohol, and 10 ml. of water was added dropwise at 5°–15° C., 6.8 grams (0.0885 mole) of carbon bisulfide and stirring continued at 25°–30° C. for an hour. Thereupon there was added in one portion 23 grams (0.0885 mole) of the N-chloroacetyl-N'-phenyl-p-phenylenediamine described above. The reaction mixture was heated at 50°–60° C. for 5 hours and at 25°–30° C. for 18 hours, 600 ml. of water then added, the mixture cooled to 0° C., and stirred at 0°– ° C. for an hour. The precipitate was collected by filtration, washed with water until the washings were neutral to litmus, and air-dried at 25°–30° C. [(p-Anilinophenyl)carbamoyl]-methyl 3-azabicyclo[3.2.2]nonane-3-carbodithioate was obtained in 92% yield as a light tan solid melting at 151°–152° C. after recrystallization from alcohol. Analysis gave 9.46% nitrogen and 15.28% sulfur compared to 9.87% nitrogen and 15.07% sulfur caculated for $C_{23}H_{27}N_3OS_2$.

EXAMPLE 50

N-Chloroacetyl-N-isopropyl-N'-phenyl-p-phenylenediamine was required as a starting material in this example. A mixture of 45.2 grams (0.2 mole) of N-isopropyl-N'-phenyl-p-phenylenediamine, 20.3 grams (0.2 mole) of triethylamine, and 500 ml. of ethyl ether was prepared and 22.6 grams (0.2 mole) of chloroacetyl chloride added dropwise at 25°–30° C. with ice-cooling. Stirring was continued at 25°–30° C. for 24 hours, 500 ml. of water added, and stirring continued for 30 minutes at the same temperature. The precipitate was collected by filtration washed with water until the washings were neutral to litmus, and air-dried at 25°–30° C. The product was obtained in 75% yield melting at 159°–161° C. after recrystallization from benzene.

To a stirred solution containing 8.3 grams (0.0665 mole) of amine, 4.4 grams (0.0665 mole) of 85% potassium hydroxide, 300 ml. of acetone, and 10 ml. of water was added dropwise at 5°–15° C., 5.1 grams (0.0665 mole) of carbon bisulfide. After stirring for an hour at 25°–30° C., 20 grams (0.0665 mole) of the N-chloroacetyl-N-isopropyl-N'-phenyl-p-phenylenediamine described above was added in one portion and the mixture heated at 55°–56° C. for 5 hours and at 25°–30° C. for 18 hours. Thereupon, there was added 600 ml. of water and the mixture stirred at 0°–10° C. for an hour. The precipitate was collected by filtration, washed with water until the washings were neutral to litmus, and air-dried at 25°–30° C. [(p-Anilinophenyl)isopropylcarbamoyl]methyl 3-azabicyclo[3.2.2]nonane-3-carbodithioate was obtained in 94% yield as a dark grey solid melting at 189°–190° C. after recrystallization from alcohol. Analysis gave 8.94% nitrogen and 13.46% sulfur compared to 8.99% nitrogen and 13.71% sulfur calculated for $C_{26}H_{33}N_3OS_2$.

EXAMPLE 51

To a stirred solution containing 31.3 grams (0.25 mole) of amine, 40 grams (0.25 mole) of 25% sodium hydroxide, and 1200 ml. of ethyl alcohol was added dropwise at 5°–15° C., 18 grams (0.25 mole) of carbon bisulfide. After stirring at 25°–30° C. for an hour, 50.6 gram (0.25 mole) of 2,4-dinitrochlorobenzene was added in one portion and the mixture heated at reflux for 5 hours. After cooling to 25° C., 2000 grams of ice-water was added and stirring continued at 25°–30° C. for an hour. 2,4Dinitrophenyl 3-azabicyclo[3.2.2-]nonane-3-carbodithioate was isolated as described in Example 50. It was obtained in 97% yield as a yellow solid melting at 158°–159° C. after recrystallization from ethyl acetate. Analysis gave 11.14% nitrogen and 17.36% sulfur compared to 11.44% nitrogen and 17.47% sulfur calculated for $C_{15}H_{17}N_3O_4S_2$.

EXAMPLE 52

To a stirred solution containing 25 grams (0.2 mole) of amine, 20.3 grams (0,2 mole) of triethyl amine and 700 ml. of ethyl ether was added dropwise at 5°–15° C., 15.2 grams (0.2 mole) of carbon bisulfide and the mixture stirred at 25°–30° C. for an hour. After cooling to 5° C., 37.2 grams (0.2 mole) of perchloromethyl mercaptan in 100 ml. of ethyl ether was added dropwise over a period of 30 minutes at 5°–10° C. After stirring at 0°–10° C. for 2hours, the by-product precipitate collected by filtration was washed with 100 ml. of ethyl ether and the precipitate discarded. The ether was removed in vacuo at a maximum temperature of 30° C. 1–2 mm. and the resulting solid dried on a porous plate. Trichloromethyl trithioperoxy-3-azabicylco[3.2.2]nonane-3-carbodithioate was obtained in 22.8% yield as a tan solid melting at 94°–95° C. after recrystallization from heptane. Analysis gave 4.00% nitrogen and 29.59% chlorine compared to 3.99% nitrogen and 30.32% chlorine calculated for $C_{10}H_{14}Cl_3NS_3$.

EXAMPLE 53

To a stirred solution containing 25 grams (0.2 mole) of amine, 32 grams (0.2 mole) of 25% sodium hydroxide and 300 ml. of water was added dropwise at 5°–15° C., 15.2 grams (0.2 mole) of carbon bisulfide. After stirring at 25°–30° C. for an hour, 20.6 grams (0.2 mole) of 2-butadienyl methyl chloride was added in one portion and stirring continued at 25°–30° C. for 24 hours. The reaction mixture was then extracted with 500 ml. of ethyl ether, the ether solution separated, washed with water until the washings were neutral to litmus, and dried over sodium sulfate. The ether was removed in vacuo at a maximum temperature of 80°–90° C./1–2 mm. 2-Methylene-3-butenyl 3-azabicyclo[3.2.2]nonane-3-carbodithioate was obtained in 98.2% yield as a viscous amber oil. Analysis gave 5.22% nitrogen and 23.30% sulfur compared to 5.24% nitrogen and 23.98% sulfur calculated for $C_{14}H_{21}NS_2$.

EXAMPLE 54

Bis(3-azabicyclo[3.2.2]non-3-ylthiocarbonyl) disulfide was required as a starting material in this example. A mixture of 25 grams (0.2 mole) of amine, 32 grams (0.2 mole) of 25% sodium hydroxide, and 500 ml. of water was prepared and 15.2 grams (0.2 mole) of carbon bisulfide added dropwise at 5°–15° C. After stirring the mixture at 25°–30° C. for an hour, the solution was cooled to 5° C. and 25.2 grams (0.11 mole) of $(NH_4)_2S_2O_8$ dissolved in 100 ml. of water added dropwise at 0°–10° C. in an hour. The reaction mixture was held at 0°–10° C. for an additional hour, the precipitate then collected by filtration, washed with water until the washings were neutral to litmus, and air-dried at 25°–30° C. The product was obtained in 90% yield as a white solid melting at 174°–182° C. After recrystallization with dimethylformamide it melted at 183°–185° C.

A mixture of 100.2 grams of the bis(3-azabicyclo[3.2.2]-non-3-ylthiocarbonyl) disulfide described above, 200 grams (2.0 mole, 200% excess) of hexamethylenimine and 600 ml. of isopropyl alcohol was stirred at 45°–50° C. for 3 hours. Thereupon, there was added dropwise at 45°–50° C. in 2 hours 0.375 mole of sodium hypochlorite (50% excess) in the form of 170 ml. of solution containing 16.4 grams hypochlorite per 100 ml. The reaction mixture was held at 45°–50° C. for an additional hour and 300 ml. isopropyl alcohol then added. The mixture was heated to 80° C. in 15 minutes and filtered hot to remove a small amount of impurities. The filtrate was added to 4000 grams of ice-water containing 5 grams of sodium sulfite and stirred at 0°–10° C. for an hour. The precipitate was collected by filtration, washed with water until the washings were neutral to litmus, and air-dried at 25°–30° C. Hexahydroazapin-1-yl azabicyclo[3.2.2]nonane-3-carbodithioate was obtained in 70.5% yield as a brown solid melting at 102°–104° C. after recrystallization from ethyl acetate. Analysis gave 9.30% nitrogen and 21.56% sulfur compared to 9.39% nitrogen and 21.48% sulfur calculated for $C_{15}H_{26}N_2S_2$.

EXAMPLE 55

To a stirred mixture containing 60 grams (0.4 mole) of amine, 26.4 grams (0.4 mole) of 85% potassium hydroxide, 500 ml. of acetone, and 20 ml. of water was added dropwise at 5°–15° C., 30.4 grams (0.4 mole) of carbon bisulfide. After stirring at 25°–30° C. for an hour, 31.4 grams (0.2 mole) of ethyl dichloroacetate was added in one portion, causing the temperature to rise from 25° C. to 47° C. The mixture was stirred at 25°–30° C. for 24 hours, 500 ml. of water added, and the solution cooled to 0° C. The precipitate was collected by filtration, washed with water until the washings were neutral to litmus, and air-dried at 25°–30° C. Ethyl dimercaptoacetate, bis(3-azabicyclo[3.2.2]nonane-3-carbodithioate was obtained in 99% yield as a white solid melting at 185°–186° C. after recrystallization from ethyl acetate/chloroform. Analysis gave 5.64% nitrogen and 26.30% sulfur compared to 5.76% nitrogen and 26.35% sulfur calculated for $C_{22}H_{34}N_2O_2S_4$.

EXAMPLE 56

The intermediate, bis(3-azabicyclo[3.2.2]non-3-yl-thiocarbonyl) disulfide, was prepared substantially as described in the first paragraph of Example 54. The charge consisted of 125 grams (1.0 mole) of amine, 160 grams (1.0 mole) of 25% sodium hydroxide, 2000 ml. of water, 76 grams (1.0 mole) of carbon bisulfide, and 156 grams (0.55 mole) of $(NH_4)_2S_2O_8$ dissolved in 1000 ml. of water. The product was obtained in 97.5% yield melting at 183°–185° C. after recrystallization from dimethyl formamide. Analysis gave 7.17% nitrogen and 31.63% sulfur compared to 6.99% nitrogen and 32.01% sulfur calculated for $C_{18}H_{28}N_2S_4$.

A slurry was prepared employing 40 grams (0.1 mole) of the intermediate described above, 7.4 grams (0.1 mole) of 96% potassium cyanide, and 550 ml. of water and stirred at 25°–30° C. for 5 hours. The precipitate was collected by filtration, washed with one liter of water, and air-dried at 25°–30° C. Bis(3-azabicyclo[3.2.2]non-3-ylthiocarbonyl) sulfide was obtained in 92.5% yield as a yellow solid melting at 159°–160° C. after recrystallization from ethyl acetate. Analysis gave 7.47% nitrogen and 26.54% sulfur compared to 7.60% nitrogen and 26.10% sulfur calculated for $C_{18}H_{28}N_2S_3$.

EXAMPLE 57

To a stirred solution containing 25 grams (0.2 mole) of amine, 13.2 grams (0.2 mole) of 85% potassium hydroxide, 300 ml. of acetone, and 10 ml. of water was added dropwise at 5°–15° C., 15.2 grams (0.2 mole) of carbon bisulfide. After stirring at 25°–30° C. for an hour, 34 grams (0.1 mole) of $S(CH=CClCH_2Br)_2$ was added in one portion causing the temperature to rise from 25° C. to 40° C. The mixture was stirred at 25°–30° C. for 24 hours, 500 ml. of water and 100 ml. of ethyl ether added, and stirring continued at 25°–30° C. for 30 minutes. The precipitate was collected by filtration, washed with water until the washings were neutral to litmus, and air-dried at 25°–30° C. The 3,3'-Thiobis(2-chloro-2-propane-1-thiol)bis(3-azabicyclo[3.2.2]nonane-3-carbodithioate) was obtained in 60% yield as a brown solid melting at 94°–96° C. after recrystallization from ethyl acetate. Analysis gave 4.83% nitrogen and 27.43 sulfur compared to 4.82% nitrogen and 27,56% sulfur calculated for $C_{24}H_{34}Cl_2N_2S_5$.

EXAMPLE 58

The sodium salt of the 3-azabicyclo[3.2.2]nonane-3-carbodithioic acid was prepared by mixing together 12.5 grams (0.1 mole) of amine, 16 grams (0.1 mole) of 25% sodium hydroxide, and 300 ml. of water. Thereupon with stirring there was added, dropwise at 5°–15° C., 7.6 grams (0.1 mole) of carbon bisulfide and stirring continued at 25°–30° C. for 2 hours. A yield of 100% of a 6.61% aqueous solution was obtained.

EXAMPLE 59

The amine salt was prepared by reacting 0.2 mole of amine in 300 ml. of ethyl ether with 0.1 mole of carbon bisulfide. The carbon bisulfide was added to the amine dropwise at 5°–15° C. and the mixture stirred at 25°–30° C. for 3 hours. The precipitate was collected by filtration and air-dried at 25°–30° C. The 3-azabicyclo[3.2.2]nonane salt of 3-azabicyclo[3.2.2]nonane-3-carbodithioic acid was obtained in 98% yield as a white solid melting at 186°–188° C. Analysis gave 8.59% nitrogen and 19.70% sulfur compared to 8.58% nitrogen and 19.64% sulfur calculated for $C_{17}H_{30}N_2S_2$.

EXAMPLE 60

To a stirred solution containing 12.5 grams (0.1 mole) of amine, 200 ml. of acetone in 10 ml. of water, and 6.6 grams (0.1 mole) of 85% potassium hydroxide was added dropwise at 5°–15° C., 7.6 grams (0.1 mole) of carbon bisulfide and the mixture stirred at 25°–30° C. for an hour. Thereupon there was added in one portion 16.6 grams (0.1 mole) of 2-bromoethyl isothiocyanate causing a temperature rise from 28° to 37° C. The product was stirred at 25°–30° C. for 24 hours, 600 ml. of water added, and stirring continued for 30 minutes. The precipitate was collected by filtration, washed with water until the washings were neutral to litmus, and air-dried at 25°–30° C. 2-Isothiocyanatoethyl 3-azabicyclo[3.2.2]nonane-3-carbodithioate was obtained in 98% yield as a cream solid melting at 72°–73° C. after recrystallization from alcohol. Analysis gave 9.75% nitrogen and 33.19% sulfur compared to 9.78% nitrogen and 33.58% sulfur calculated for $C_{12}H_{18}N_2S_3$.

EXAMPLE 61

To a stirred solution containing 25 grams (0.2 mole) of amine, 13.2 grams (0.2 mole) of 85% potassium hydroxide and 250 ml. of ethyl alcohol in 10 ml. of water was added dropwise at 5°–15° C., 15.2 grams (0.2 mole) of carbon bisulfide. After stirring at 25°–30° C. for an hour, 17.5 grams (0.1 mole) of 1,3-di(chloromethyl)benzene was added in one portion, the product then heated at 50°–60° C. for 6 hours and at 25°–30° C. for 18 hours. Thereupon there was added 600 ml. of water and the reaction mixture stirred at 25°–30° C. for 30 minutes. The precipitate was collected by filtration, washed with water until the washings were neutral to litmus, and air-dried at 25°–30° C. 1,3-Phenyl methylenebis (3-azabicyclo[3.2.2]nonane-3-carbodithioate) was obtained in 93.5% yield as a white solid melting at 133°–135° C. after recrystallization from benzene/heptane solution. Analysis gave 5.15% nitrogen and 25.12% sulfur compared to 5.55% nitrogen and 25.41% sulfur calculated for $C_{26}H_{36}N_2S_4$.

EXAMPLE 62

Replacing the 1,3-di(chloromethyl)benzene of Example 60 with an equimolar amount of di(chloromethyl)durene, 1,4-(2,3,5,6-tetramethyl)phenyl methylenebis (3-azabicyclo[3.2.2]nonane-3-carbodithioate) was obtained in 98% yield as a white solid metting at 255°–256° C. after recrystallization from benzene. Analysis gave 4.60% nitrogen compared to 4.99% nitrogen calculated for $C_{30}H_{44}N_2S_4$.

Useful properties for accelerating the vulcanization of rubber are illustrated by the following test. A base stock was compounded comprising:

|  | Parts by Weight |
|---|---|
| Smoked sheets rubber | 100.0 |
| Carbon black | 50.0 |
| Zinc oxide | 5.0 |
| Stearic acid | 3.0 |
| Saturated hydrocarbon softener | 3.0 |
| Sulfur | 2.5 |

To each of several portions of the base stock was added 0.5 part by weight of accelerator as indicated below:

| Stock | |
|---|---|
| A | 6-Ethoxy-2-benzothiazolyl 3-azabicyclo[3.2.2]nonane-3-carbodithioate |
| B | 2-Benzothiazolyl 3-azabicyclo[3.2.2]nonane-3-carbodithioate |
| C | Ethyl 2-mercapto-4-methyl-5-thiazolecarboxylate, 3-azabicyclo[3.2.2]nonane-3-carbodithioate |
| D | 4-Methyl-2-thiazolyl 3-azabicyclo[3.2.2]nonane-3-carbodithioate |
| E | 6-Nitro-2-benzothiazolyl 3-azabicyclo[3.2.2]nonane-3-carbodithioate |
| F | 5-Chloro-2-benzothiazolyl 3-azabicyclo[3.2.2]nonane-3-carbodithioate |
| G | 5-Carbamoyl-4-methyl-2-thiazolyl 3-azabicyclo[3.2.2]-nonane-3-carbodithioate |
| H | 5-Acetyl-4-methyl-2-thiazolyl 3-azabicyclo[3.2.2]nonane-3-carbodithioate |
| J | 4-Methyl-5-(phenylcarbamoyl)-2-thiazolyl 3-azabicyclo-[3.2.2]nonane-3-carbodithioate |
| K | 2-Benzimidazolyl 3-azabicyclo[3.2.2]nonane-3-carbodithioate |
| L | 2-Benzoxazolyl 3-azabicyclo[3.2.2]nonane-3-carbodithioate |

-continued

| Stock | |
|---|---|
| M | 4,6-Dimethyl-2-pyrimidinyl 3-azabicyclo[3.2.2]nonane-3-carbodithioate |
| N | 2-(Diethylamino)ethyl 3-azabicyclo[3.2.2]nonane-3-carbodithioate |
| P | 2-Propynyl 3-azabicyclo[3.2.2]nonane-3-carbodithioate |
| Q | Phthalimidomethyl 3-azabicyclo[3.2.2]nonane-3-carbodithioate |

The stocks were cured in the usual manner by heating in a press for different periods of time at 144° C. Processing safety of the vulcanizable stocks was evaluated by means of a Mooney plastometer. The figures recorded were the times required for the Mooney plasticity at 135° C. to rise five points above the minimum value. The modulus and tensile properties at optimum cure are recorded. Hereinafter "modulus" means modulus of elasticity in pounds per square inch at 300% elongation, and "tensile" means tensile strength at break in pounds per square inch.

TABLE I

| Stock | Optimum Cure in Minutes | Modulus | Tensile | Mooney Scorch |
|---|---|---|---|---|
| A | 45 | 2890 | 3900 | 11.4 |
| B | 45 | 3100 | 4200 | 11.7 |
| C | 45 | 3130 | 4100 | 12.5 |
| D | 45 | 3410 | 4000 | 11.8 |
| E | 60 | 3490 | 3600 | 11.1 |
| F | 45 | 3000 | 4100 | 11.5 |
| G | 45 | 2620 | 3500 | 9.8 |
| H | 45 | 3120 | 3800 | 10.8 |
| J | 45 | 2600 | 3700 | 12.2 |
| K | 45 | 2150 | 3400 | 10.4 |
| L | 45 | 2170 | 3500 | 11.4 |
| M | 45 | 2550 | 3800 | 10.1 |
| N | 60 | 2330 | 3300 | 11.0 |
| P | 45 | 1880 | 3000 | 9.7 |
| Q | 60 | 1620 | 2400 | 9.5 |

As further illustrative of the invention, natural rubber tread stocks were compounded comprising:

| | Parts by Weight |
|---|---|
| Smoked sheet rubber | 100.0 |
| Carbon black | 50.0 |
| Zinc oxide | 5.0 |
| Stearic acid | 3.0 |
| Saturated hydrocarbon softener | 3.0 |
| Sulfur | 2.5 |
| Antioxidant | 1.0 |
| Accelerator | 0.5 |

The accelerator added to the base stock is indicated below:

| Stock | |
|---|---|
| R | 2-(Hexahydro-1H-azepin-1-yl)-2-oxoethyl 3-azabicyclo-[3.2.2]nonane-3-carbodithioate |
| S | Ethyl dimercaptoacetate, bis(3-azabicyclo[3.2.2]nonane-3-carbodithioate) |
| T | 2-Methylene-3-butenyl 3-azabicyclo[3.2.2]nonane-3-carbodithioate |
| U | 2,4-Dinitrophenyl 3-azabicyclo[3.2.2]nonane-3-carbodithioate |
| V | 3-Azabicyclo[3.2.2]nonane 3-azabicyclo[3.2.2]nonane-3-carbodithioate |
| W | Bis(3-azabicyclo[3.2.2]non-3-ylthiocarbonyl) disulfide |
| X | Bis(3-azabicyclo[3.2.2]non-3-ylthiocarbonyl) sulfide |

The compositions were vulcanized by heating for different periods of time in the usual manner in a press at 144° C. The accelerating properties at optimum cure and processing safety are recorded in Table II.

TABLE II

| Stock | Optimum Cure in Minutes | Modulus | Tensile | Mooney Scorch |
|---|---|---|---|---|
| R | 60 | 1140 | 2000 | 15.5 |
| S | 60 | 2300 | 3700 | 7.8 |
| T | 60 | 1250 | 2000 | 17.6 |
| U | 55 | 1970 | 3000 | 14.0 |
| V | 45 | 2380 | 3900 | 3.1* |
| W | 45 | 2590 | 3820 | 4.5* |
| X | 60 | 2630 | 4150 | 6.0* |

*Minutes to 10-point rise

Another characteristic test was carried out employing less sulfur and more antioxidant in the stock. As the formulation, there was employed 100 parts of smoked sheet rubber, 50 parts of carbon black, 5 parts of zinc oxide, 3 parts of stearic acid, 3 parts of saturated hydrocarbon softener, 2 parts of sulfur, 2 parts of antioxidant and 0.5 part of hexahydroazapin-1-yl azabicyclo[3.2.2]nonane-3-carbodithioate. After curing the stock in the usual manner in a press at 144° C., the modulus of elasticity at 300% elongation was 2460 and the tensile at break was 3600 lbs/in$^2$ at the optimum cure of 20 minutes.

In a similar manner, the new compounds were tested as vulcanization accelerators in a synthetic tire tread stock. Butadiene-styrene copolymer rubber was blended in a standard formula as follows:

| | Parts by weight |
|---|---|
| SB-R 1500 | 100.0 |
| Carbon black (high abrasion furnace) | 50.0 |
| Zinc oxide | 4.0 |
| Stearic acid | 2.0 |
| Saturated hydrocarbon softener (Nectol 60) | 10.0 |
| Sulfur | 1.75 |
| Antioxidant | 1.0 |

The accelerator was added to the stock in molecularly equivalenet amount employing 0.0045 mole of each accelerator.

| Stock | |
|---|---|
| AA | 2-Benzothiazolyl 3-azabicyclo[3.2.2]nonane-3-carbodithioate |
| BB | 6-Ethoxy-2-benzothiazolyl 3-azabicyclo[3.2.2]nonane-3-carbodithioate |
| CC | 5-Chloro-2-benzothiazolyl 3-azabicyclo[3.2.2]nonane-3-carbodithioate |
| DD | Ethyl 2-mercapto-4-methyl-5-thiazolecarboxylate, 3-azabicyclo[3.2.2]nonane-3-carbodithioate |
| EE | 4-Methyl-2-thiazolyl 3-azabicyclo[3.2.2]nonane-3-carbodithioate |
| FF | 2-Benzoxazolyl 3-azabicyclo[3.2.2]nonane-3-carbodithioate |
| GG | 2-Benzimidazolyl 3-azabicyclo[3.2.2]nonane-3-carbodithioate |
| HH | 6-Nitro-2-benzothiazolyl 3-azabicyclo[3.2.2]nonane-3-carbodithioate |
| JJ | 4,6-Dimethyl-2-pyrimidinyl 3-azabicyclo[3.2.2]nonane-3-carbodithioate |
| KK | 5-Carbamoyl-4-methyl-2-thiazolyl 3-azabicyclo[3.2.2]-nonane-3-carbodithioate |
| LL | 5-Acetyl-4-methyl-2-thiazolyl 3-azabicyclo[3.2.2]nonane-3-carbodithioate |

The compositions were vulcanized by heating for different periods of time in the usual manner in a press at 144° C. The modulus and tensile properties of the 60-minute cures are recorded below except for Stock JJ for which properties of the 45-minute cure are recorded. The time required for the Mooney plasticity at 135° C. to rise 5 points above the minimum value are also set forh.

TABLE III

| Stock | Modulus | Tensile | Mooney Scorch |
|---|---|---|---|
| AA | 1800 | 3700 | 24.4 |
| BB | 1700 | 3700 | 25.6 |
| CC | 1520 | 3600 | 26.5 |
| DD | 1600 | 3300 | 28.4 |
| EE | 2160 | 3400 | 23.5 |
| FF | 1420 | 3600 | 16.2 |
| GG | 1550 | 3800 | 13.9 |
| HH | 1540 | 3600 | 23.1 |
| JJ | 2110 | 3400 | 14.4 |
| KK | 1950 | 3200 | 22.2 |
| LL | 1800 | 3200 | 23.7 |

Higher curing temperatures may be employed. To the butadiene-styrene copolymer rubber standard formula above was added 1.0 part of ethyl dimercaptoacetate, bis(3-azabicyclo[3.2.2]nonane-3-carbodithioate) and the stock cured at 153° C. After heating 75 minutes at 153° C. the stock developed a tensile strength of 3400 pounds per square inch.

To demonstrate the effectiveness of the accelerators of this invention in cis-polybutadiene, the rubber was compounded by milling together the ingredients in the following base formula:

| | Parts by weight |
|---|---|
| Cis-1,4-polybutadiene | 100.0 |
| Aromatic oil softener | 10.0 |
| Carbon black (high abrasion furnace) | 50.0 |
| Zinc oxide | 3.0 |
| Stearic acid | 2.0 |
| Sulfur | 1.75 |

To the above there was added in separate stocks a molecularly equivalent amount of accelerator as follows:

| Stock | |
|---|---|
| MM | 2-Benzothiazolyl 3-azabicyclo[3.2.2]nonane-3-carbodithioate |
| NN | 2-Benzoxazolyl 3-azabicyclo[3.2.2]nonane-3-carbodithioate |
| OO | 2-Benzimidazolyl 3-azabicyclo[3.2.2]nonane-3-carbodithioate |

The stocks were vulcanized by heating in a press for different periods of time at 144° C. The vulcanizates were tested for stress, tensile strength, and hardness. The results at optimum cure are recorded.

TABLE IV

| Stock | Optimum Cure in Minutes | Modulus | Tensile | Hardness |
|---|---|---|---|---|
| MM | 45 | 1400 | 1900 | 61 |
| NN | 45 | 950 | 1900 | 60 |
| OO | 30 | 1200 | 2500 | 60 |

Examples of the present invention were also tested in a rubber stock containing a nitroso compound as a vulcanization retarder. The base stock employed was as follows:

| | Parts by Weight |
|---|---|
| Smoked sheets rubber | 100.0 |
| Carbon black | 50.0 |
| Zinc oxide | 5.0 |
| Stearic acid | 3.0 |
| Saturated hydrocarbon softener | 3.0 |
| Sulfur | 2.5 |
| N-Nitroso diphenylamine | 1.0 |
| Accelerator | 0.5 |

The accelerator added to the base stock is indicated below:

| Stock | |
|---|---|
| PP | 2-Benzothiazolyl 3-azabicyclo[3.2.2]nonane-3-carbodithioate |
| QQ | 2-Benzoxazolyl 3-azabicyclo[3.2.2]nonane-3-carbodithioate |
| RR | 2-Benzimidazolyl 3-azabicyclo[3.2.2]nonane-3-carbodithioate |
| SS | 4,6-Dimethyl-2-pyrimidinyl 3-azabicyclo[3.2.2]nonane-3-carbodithioate |

Vulcanization was completed at a temperature of 144° C. The modulus and tensile properties of the 30-minute cures and processing safety are recorded in Table V.

TABLE V

| Stock | Modulus | Tensile | Mooney Scorch Time at 135° C. In Minutes for 5-Point Rise Above Minimum |
|---|---|---|---|
| PP | 3080 | 4300 | 19.4 |
| QQ | 2490 | 3700 | 16.3 |
| RR | 2050 | 3600 | 14.3 |
| SS | 3010 | 4100 | 15.9 |

As a specific embodiment of the invention illustrating the antidegradant properties, a rubber base composition was compounded comprising:

| | Parts by Weight |
|---|---|
| Smoked sheet rubber | 100.0 |
| Carbon black | 50.0 |
| Zinc oxide | 5.0 |
| Stearic acid | 3.0 |
| Saturated hydrocarbon softener | 3.0 |
| Sulfur | 2.5 |
| Accelerator | 0.5 |

To the base composition was added 3.0 parts by weight of antidegradant and the composition cured by heating in a press for different periods of time at 144° C. The stocks at optimum cure were then aged for 48 hours at 100° C. by the test tube method (A.S.T.M. designation D865-57, A.S.T.M. Standards, 1958, p. 1453).

TABLE VI

| Antidegradant | Optimum Cure in Minutes | % Retention of Ultimate Tensile Strength |
|---|---|---|
| None | 50 | 26 |
| [(p-Anilinophenyl)carbamoyl]methyl 3-azabicyclo[3.2.2]nonane-3-carbodithioate | 25 | 75 |
| [(p-Anilinophenyl)isopropylcarbamoyl]methyl 3-azabicyclo[3.2.2]nonane-3-carbodithioate | 40 | 58 |

Stress relaxation measurements afforded another important demonstration of antidegradant properties. A weight was affixed to one end of a cured strip of rubber, the other end of which was maintained in fixed position. Gradual relaxation of stress was followed by periodically measuring the elongation. The time for elongation to increase 100% was recorded. This test, commonly referred to as creep test, furnishes a reliable indication of fugitiveness of an antidegradant. The applied load was 45 pounds per square inch to the above stocks.

TABLE VII

| Antidegradant | Creep - Hours to 100% Increase in Elongation |
|---|---|
| None | 57 |
| [(p-Anilinophenyl)carbamoyl]methyl 3-azabicyclo-[3.2.2]nonane-3-carbodithioate | 250 |
| [(p-Anilinophenyl)isopropylcarbamoyl]methyl 3-azabicyclo[3.2.2]nonane-3-carbodithioate | 142 |

It is intended to cover all changes and modifications of the samples of the invention herein chosen for purposes of disclosure which do not constitute departures from the spirit and scope of the invention.

What is claimed is:

1. A compound of the formula

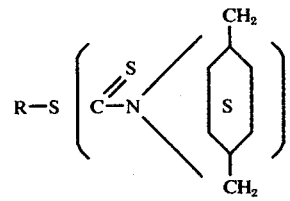

where R is selected from a group consisting of $-SCCl_3$, $Y-S_x$ where $x$ is an integer from 0 to 3, inclusive, and Y is the radical in parentheses,
lower alkyl,
cyano lower alkyl,
isothiocyano lower alkyl,
amino lower alkyl where amino is $NH_2$, lower alkyl NH—, (lower alkyl)$_2$N-, 1-pyrrolidinyl, piperidino, morpholino, or 1-hexamethyleniminyl,
lower alkenyl,
halogen-substituted lower alkenyl,
cyclohexenyl,
alkadienyl of 6 to 10 carbon atoms
aryl where aryl is phenyl or naphthyl and substituted aryl where aryl has the same meaning as before and is substituted by one or more lower alkyl, halogen or nitro,
arylthio lower alkyl and substituted arylthio lower alkyl where aryl and substituted aryl have the same meaning as before
lower alkynyl,
aryl lower alkyl and substituted aryl lower alkyl where aryl has the same meaning as before and the substituents are one or more selected from the group consisting of $-CH_2SY$ where Y has the same meaning as before, halogen, lower alkyl and nitro,
furyl lower alkyl,
pyranyl lower alkyl,
5-hydroxy pyranonyl lower alkyl,
2-phenyleneazolyl and substituted 2-phenyleneazolyl
wherein phenyleneazolyl is benzothiazolyl, benzoxazolyl, or benzimidazolyl, and the substituents are lower alkyl, chloro, nitro, or lower alkoxy, substituted 2-thiazolyl wherein the substituents are lower alkyl, lower alkoxy carbonyl, carbamyl, anilino carbonyl or acetyl 2-pyrimidinyl, 2-pyrimidinyl containing one or two lower alkyl substituents, phthalazinyl, imidomethyl wherein imido is phthalimido, succinimido, maleimido or tetrahydrophthalimido, —CH(SY)C(O)R', and —CH$_2$C(O)R' where Y has the same meaning as before and R' is lower alkoxy or amino; where amino is NH$_2$, mono-lower alkylamino, di(lower alkyl)amino, 3-azabicyclo(3.2.2) non-3yl, 1-pyrrolidinyl, piperidino, morpholino, 1-hexamethyleniminyl, N-phenyl-N-lower alkylamino, N-(4-anilinophenyl)amino and N-lower alkyl-N-(4-anilinophenyl)amino;

ammonium, alkali metal, alkaline-earth metal, zinc, copper, lead, and iron;

substituted ammonium selected from the group consisting of:

mono(lower alkyl) ammonium, di(lower alkyl) ammonium, tri(lower alkyl) ammonium, cyclohexyl ammonium, dicyclohexyl ammonium, pyrrolidinium, piperidinium, hexamethyleniminium, morpholinium, 3-azoniabicyclo(3.2.2) nonane, N,N-di(lower alkyl) cyclohexylammonium, N,N-di(lower alkyl) N-phenylammonium, and triethanol ammonium.

2. A compound of claim 1 where R is amino lower alkyl.

3. A compound of claim 1 where R is substituted ammonium.

4. A compound of the formula

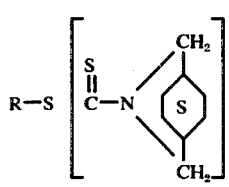

where R is alkali metal.

5. A compound of the formula

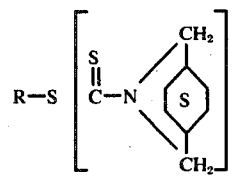

where R is Y — S$_x$ where Y is the radical in parentheses and $x$ is an integer from 0 to 3, inclusive.

6. A compound of claim 1 where R is 2-phenyleneazolyl or substituted 2-phenyleneazolyl.

7. A compound of the formula

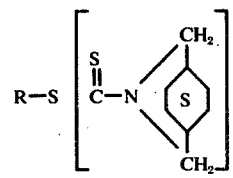

where R is N,N-di(lower alkyl)amino lower alkyl.

8. A compound of the formula

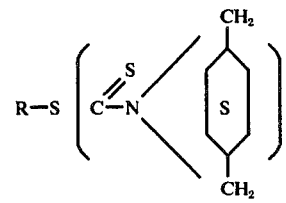

where R is 3-azoniabicyclo(3.2.2)-nonane.

9. 2-Benzothiazolyl 3-azabicyclo[3.2.2]nonane-3-carbodithioate.

10. 6-Ethoxy-2-benzothiazolyl 3-azabicyclo[3.2.2]-nonane-3-carbodithioate.

11. 4-Methyl-2-thiazolyl 3-azabicyclo[3.2.2]nonane-3-carbodithioate.

12. 6-Nitro-2-benzothiazolyl 3-azabicyclo[3.2.2]-nonane-3-carbodithioate.

13. Bis(3-azabicyclo[3.2.2]non-3-ylthiocarbonyl) disulfide.

14. Bis(3-azabicyclo[3.2.2]non-3-ylthiocarbonyl) sulfide.

15. Thio-3-azabicyclo[3.2.2]nonane-3-carbonyl chloride.

16. A compound of the formula

or

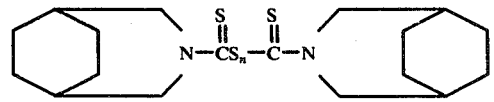

wherein R is alkali metal, alkaline earth metal, iron, zinc, or ammonium, $m$ is equal to the valence of R, and $n$ is 1–3.

* * * * *